United States Patent [19]

Bodeen

[11] 3,974,827

[45] Aug. 17, 1976

[54] PORTABLE ORTHOPEDIC DEVICE

[75] Inventor: Joseph J. Bodeen, Morgan Hill, Calif.

[73] Assignee: Benjamin T. Angileri, San Jose, Calif.

[22] Filed: May 12, 1975

[21] Appl. No.: 576,698

[52] U.S. Cl. .............................. 128/70; 128/DIG. 20; 297/284; 5/327 B
[51] Int. Cl.² ...................... A61F 5/00; A47C 27/08; A47C 27/18
[58] Field of Search .................... 128/69, 70, 78, 75, 128/DIG. 20; 297/284; 5/327 B, 327 R, 348 R

[56] References Cited
UNITED STATES PATENTS

| | | | |
|---|---|---|---|
| 2,521,530 | 9/1950 | McGuffage | 5/327 R |
| 3,326,601 | 6/1967 | Vanderbilt et al. | 297/284 |
| 3,540,776 | 11/1970 | Wilson | 297/284 X |
| 3,596,990 | 8/1971 | Gottfried et al. | 297/284 |

FOREIGN PATENTS OR APPLICATIONS

| | | | |
|---|---|---|---|
| 267,348 | 12/1968 | Austria | 297/284 |
| 1,015,989 | 8/1952 | France | 128/69 |

Primary Examiner—Ronald L. Frinks
Attorney, Agent, or Firm—William R. Piper

[57] ABSTRACT

An orthopedic device which will provide adjustable and yieldable support to the lumbar region of the spine when a person is in a sitting position. It can also provide adjustable and yieldable support to the cervical region of the spine when the person is in a supine position. It can also provide adjustable and yieldable support to the lumbar region when the person is in the supine position. The device has a semi-flexible flat backing member placed behind an air inflatable bladder so as to direct all of the varied and yielding pressures from the air inflated bladder in a forward direction and directly against the spinal column. The inflated bladder presses against a flap provided in a foam rubber front layer to permit the adjustable yielding pressure from the bladder to be distributed evenly against either the lumbar or the cervical region of the spine.

4 Claims, 5 Drawing Figures

PORTABLE ORTHOPEDIC DEVICE

SUMMARY OF THE INVENTION

An object of my invention is to provide a portable orthopedic device that is preferably square in shape and relatively thin in thickness. The device makes use of a fiberglass or other type plastic material backing with a layer of foam rubber on its rear surface and an air inflatable bladder attached to its front surface in a position where the bladder will be at the lumbar region of the spine when the device is placed at the back of a seat and the lower edge of the device is supported by the seat. One of the novel features is the provision of a flap in a front layer of foam rubber that overlies the front of the bladder, the remainder of the front layer overlying the front face of the backing. The flap permits the bladder to be air inflated to the desired degree and the flap will distribute the yielding pressure of the bladder evenly over the lumbar or cervical region of the spine, this depending upon the place where the device is positioned.

DESCRIPTION OF THE PREFERRED EMBODIMENT

Figure 5:
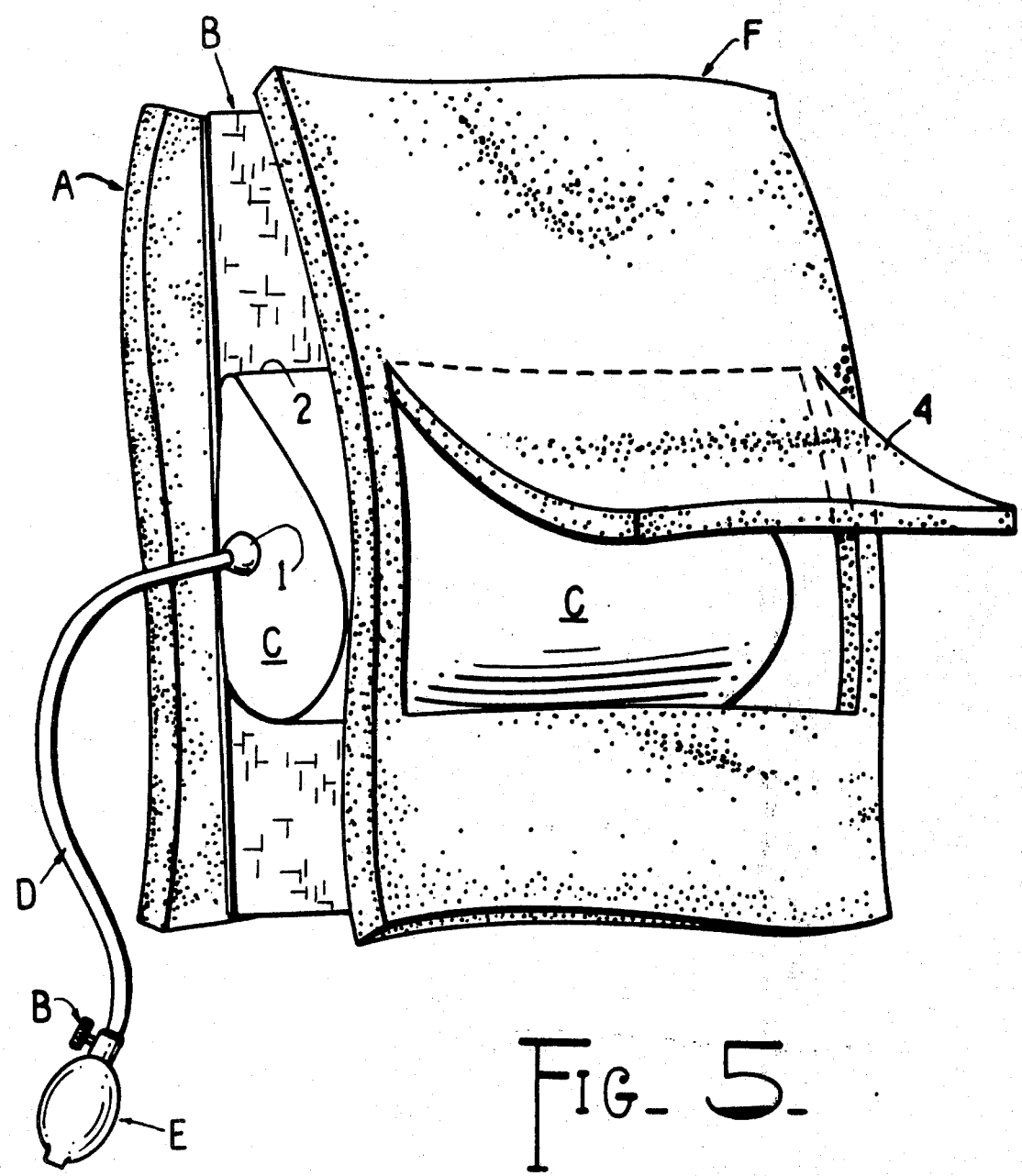
FIG. 5 is an enlarged exploded perspective view of the different parts without the cover, which encloses these parts, being shown.

In carrying out my invention I will first describe the various parts which are enclosed in a cover and then will set forth how the cover encloses these parts to provide the portable orthopedic device. FIG. 5 illustrates the various parts of the device in relation to each other and does not show the cover. The rear layer A of the device is preferably made of foam rubber that is about one-half inch thick and covers a square area of about 16 inches on each side. I do not wish to be confined to these exact measurements. The rear layer A will provide body to the orthopedic device and will add a certain degree of comfort to the one using the device. It is possible to use other types of filler material which would be flexible.

Next I provide a back support B, preferably made of a hard flexible plastic or fiber glass. This back support is positioned in front of the rear layer A and is about one-sixteenth inch thick and is square measuring about fifteen inches on each side. The rear surface of the back support is secured to the adjacent surface of the rear layer by an adhesive, not shown. The back support B is used to provide a foundation for an inflatable bladder C which will presently be described. The back support B, when secured to the rear layer A, will allow a one-half inch margin of the rear layer A all around the back support.

It is extremely important to have the back support B placed in back of the air inflatable bladder C so as to allow all or most of the air pressure build up in the bladder to exert a yielding forward thrust against the back of the person using the device. If this semi-rigid back support were not provided, most of the built up air pressure within the bladder would be dispersed toward the rear layer A of the device and would not provide the necessary pressure needed to support the lumbar region of the spine, which in turn relieves any disc pressure in the spine and the end result is the relief of the low back pain to the person. This has been significantly demonstrated by a medical study published in the Orthopedic Clinics of North America, Volume 6, No. 1, January 1975, pages 105 through 120.

The inflatable bladder C is made of rubber or vinyl and it has an air inlet/outlet 1 positioned at one of its ends. The size of the bladder preferably measures fifteen inches long and six inches wide. It is placed on the back support B so that the upper edge 2 of the bladder is about five inches down from the top edge of the back support, see FIG. 5. The length of the bladder C is equal to the width of the back support and the bladder is secured to the adjacent surface of the back support by an adhesive, not shown. The bladder may be filled with air to expand up to approximately six inches from front to back. The bladder when inflated provides a support to the lumbar region of the person's back that uses the device or the cervical region depending on how it is used.

The air inlet/outlet 1 for the bladder C, see FIG. 5, has an inside diameter of about one-fourth of an inch. A clear vinyl tubing D, about 15 inches in length with an outside diameter of about one-fourth inch, has one end inserted into the air inlet/outlet 1 and is permanently attached thereto. A standard hand held bulb E with an air valve shut off knob 3 is attached to the free end of the tubing D. The bulb E is used to inflate the bladder C and the air valve shut off knob 3 may be operated to release the air from the bladder.

A sufficient volume of air can be pumped into the bladder C by successively depressing the blub E to provide enough air pressure in the bladder to exert the desired pressure against the user's lumbar spine and thereby decrease the lumbar disc pressure and help relieve the lumbar pain. The degree of yielding pressure can be varied depending upon how much the bladder is inflated or deflated. This is very significant in order to produce the necessary pressure for different individuals. The shut-off knob 3 is opened to release the air in the bladder or when pumping air into the bladder by the successive depressing of the bulb E.

The placement of the bladder C on the back support B is also significant in order to produce the results just mentioned. The securing of the bladder to the back support by adhesive prevents the bladder from shifting when the bladder is inflated or deflated.

Referring again to FIG. 5, it will be seen that I provide a front layer F of foam rubber of the same size and thickness as the rear layer A. This front layer F differs from the rear layer A in that it is provided with an integral flap 4. The flap is formed by providing a U-shaped cut in the front layer. It is preferably about fifteen inches long and the sides are about six and one fourth inches long. This means that the side cuts of the flap 4 will be spaced about one-half inch in from the adjacent sides of the front layer. The bottom edge of the flap will be disposed the same distance above the lower edge of the front layer F, as is the lower edge of the bladder C. This will cause the lower edge of the bladder to coincide with the lower edge of the U-shaped cut forming the flap with the result that when the bladder is inflated with air it will immediately swing the flap outwardly and occupy the space formerly occupied by the flap with the exception of the top of the flap where it merges into the plane of the front layer F.

The flap 4 in the front layer F protects the bladder C from abrasion from the covering material which will be described hereinafter. The flap also affords additional comfort to the person using the device because it allows a more uniform distribution of pressure from the bladder to the lumbar spine area when the bladder is inflated. The front layer F is secured to the adjacent face of the back support with the exception of the flap 4. The flap merely covers the adjacent surface of the bladder C and is not secured to it.

The base support B with its rear layer A and front layer F together with the bladder C are enclosed in a cover G, see FIGS. 1–4 inclusive. The cover is preferably made of vinyl cushion-type material and it has an opening in its side wall through which the air inlet/outlet member 1 for the bladder C extends.

OPERATION

Figure 1:
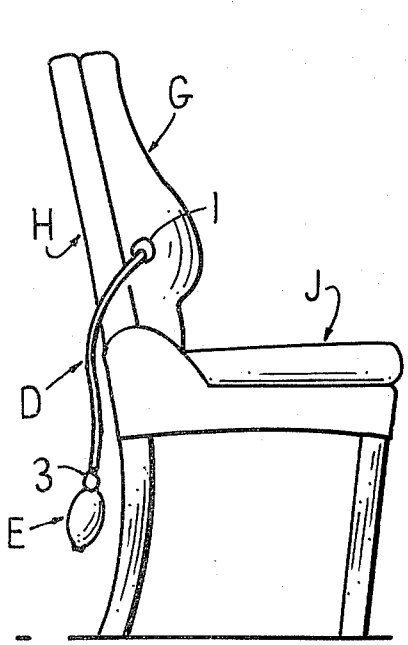
FIG. 1 is a side elevation of the portable orthopedic device when placed against the back of a chair where the chair back can be swung into different angular positions. The device has the bladder inflated.
Figure 2:
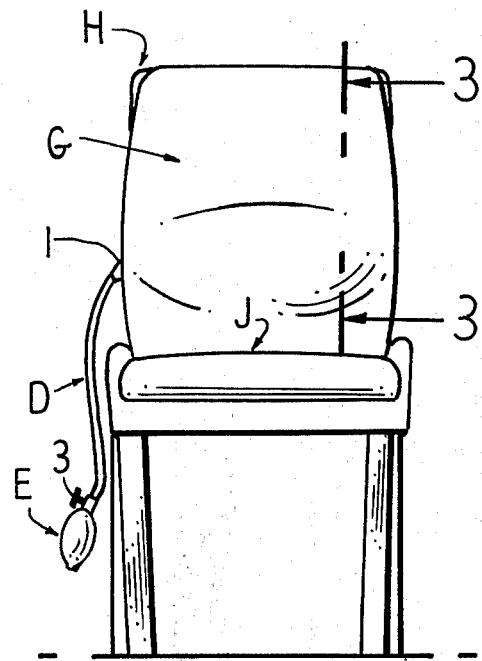
FIG. 2 is a front elevation of FIG 1.
Figure 3:
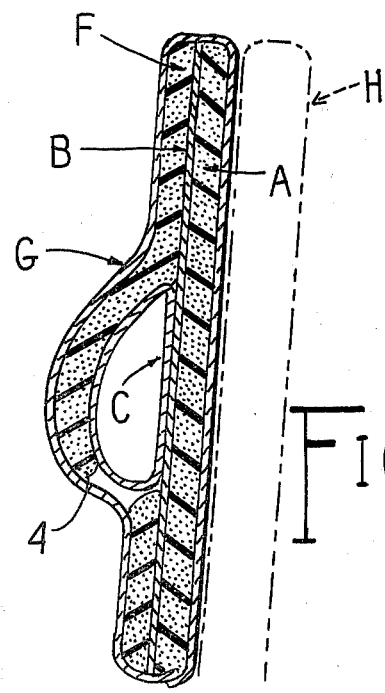
FIG. 3 is an enlarged vertical transverse section taken along the line 3—3 of FIG. 2 and shows the bladder air inflated.
Figure 4:
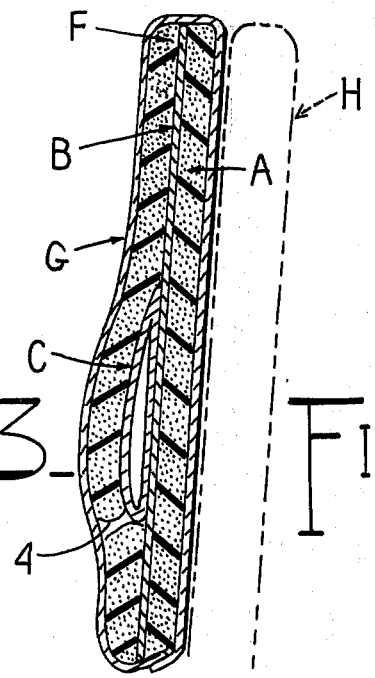
FIG. 4 is similar to FIG. 3, but shows the bladder deflated.

From the foregoing description of the various parts of the device, the operation thereof may be readily understood. FIGS. 1 and 2 show the portable orthopedic device placed against the back H of a chair with the lower edge of the device resting on the chair seat J. Such an arrangement will place the bladder C in the device in a position where it will apply the desired amount of yielding pressure when the bladder is air inflated, against the lumbar region of the spine to a person sitting in the chair and resting his back against the device or laying down in the supine position with the device under the back. The inflated bladder C will press the flap 4 outwardly against the adjacent surface of the cover G and cause the cover to buldge, as clearly seen in FIGS. 1 and 2, and to permit the yielding pressure from the bladder to be distributed evenly against the lumbar region of the spine to relieve any back pain in this region.

The portable orthopedic device can also be applied to the cervical region of the spine when a person lies supine on his back on a bed with the device placed under his head and neck so that the inflated bladder portion will apply the desired yielding pressure uniformly to the cervical region of the spine.

I claim:

1. A portable orthopedic device comprising:
   a. a flat back support made of semi-flexible material;
   b. an air inflatable bladder secured to the front surface of said back support and extending over only a portion of the front surface thereof;
   c. a front layer of a flexible compressible material covering the same area as said back support and overlying the bladder and exposed area of said support, said front layer having an integral flap overlying said bladder and being coextensive with the front surface of said bladder so that the flap will swing outwardly and permit the bladder to be inflated;
   d. a cover enclosing the back support, bladder and said front layer; and
   e. hand actuated means for pumping the desired amount of air into said bladder for inflating it to the desired extent so that the device can be placed to apply the desired yieldable pressure against the lumbar region of a person when in a sitting position or can be placed at the cervical or lumbar region to apply the desired yielding pressure when a person is in a supine position.

2. The combination as set forth in claim 1: and in which
   a. a rear layer of a flexible compressible material is positioned in back of said back support and covers the entire rear surface of said back support, said rear layer being enclosed by said cover.

3. The combination as set forth in claim 1: and in which
   a. said hand actuated means for pumping air into said bladder includes a flexible air-conveying tube communicating with the interior of said bladder and having a hand operated air bulb at its outer end with a shut-off valve.

4. The combination as set forth in claim 2: and in which
   a. the flat back support, the front layer and the rear layer are all substantially square in area and of the same size; and
   b. said bladder is substantially rectangular in shape and has a length slightly less than the width of said back support, and the lower edge of said bladder being spaced above the lower edge of said back support and lying substantially flush with the lower edge of said flap in said front layer.

* * * * *